United States Patent [19]

Springs

[11] Patent Number: 5,382,223

[45] Date of Patent: Jan. 17, 1995

[54] CONTOURED ORTHOPAEDIC SUPPORT HAVING REDUCED SKIN IRRITATION PROPERTIES

[75] Inventor: Michael A. Springs, Leawood, Kans.

[73] Assignee: Ortho-Care, Inc., Raytown, Mo.

[21] Appl. No.: 11,975

[22] Filed: Feb. 1, 1993

[51] Int. Cl.⁶ .............................. A61F 5/00; B32B 31/00
[52] U.S. Cl. ............................................ 602/6; 602/23;
602/26; 602/62; 602/63; 156/304.5; 156/217;
156/218
[58] Field of Search .................. 602/5, 6, 7, 20, 23,
602/26, 61, 62–65; 156/217, 218, 304.2, 304.5,
304.6

[56] References Cited

U.S. PATENT DOCUMENTS

| | | | |
|---|---|---|---|
| 3,415,288 | 12/1968 | Marshack | 156/218 X |
| 3,613,681 | 10/1971 | Adams | 602/63 X |
| 4,084,584 | 4/1978 | Detty | 602/26 |
| 4,320,634 | 3/1982 | Hashimoto et al. | |
| 4,388,134 | 6/1983 | Long et al. | 156/304.5 X |
| 4,446,181 | 5/1984 | Wood | 156/218 X |
| 4,961,418 | 10/1990 | McLaurin-Smith | 602/63 X |
| 5,085,210 | 2/1992 | Smith, III | 602/63 X |

FOREIGN PATENT DOCUMENTS

| | | | |
|---|---|---|---|
| 684333 | 3/1965 | Italy | 602/26 |
| 8101240 | 5/1981 | WIPO | 602/63 |

Primary Examiner—Stephen R. Crow
Assistant Examiner—Linda C. M. Dvorak
Attorney, Agent, or Firm—Hovey, Williams, Timmons & Collins

[57] ABSTRACT

An improved orthopaedic support (10) is provided in the form of an elongated, open-ended tubular body (12) having a continuous sidewall (13), with the latter presenting a recessed region (18) intermediate the ends (14, 16) for anatomically conforming with a limb joint such as a knee. The sidewall (13) is entirely free of transverse dart-defining seams at the recessed region (18). In preferred forms, the body (12) is fabricated with only a single seam (26) extending the length thereof. The body (12) is formed from fabric-faced closed cell neoprene rubber synthetic resin material, and the seam (26) is adhesively formed and covered with heat-applied seam tape (28, 30).

5 Claims, 1 Drawing Sheet

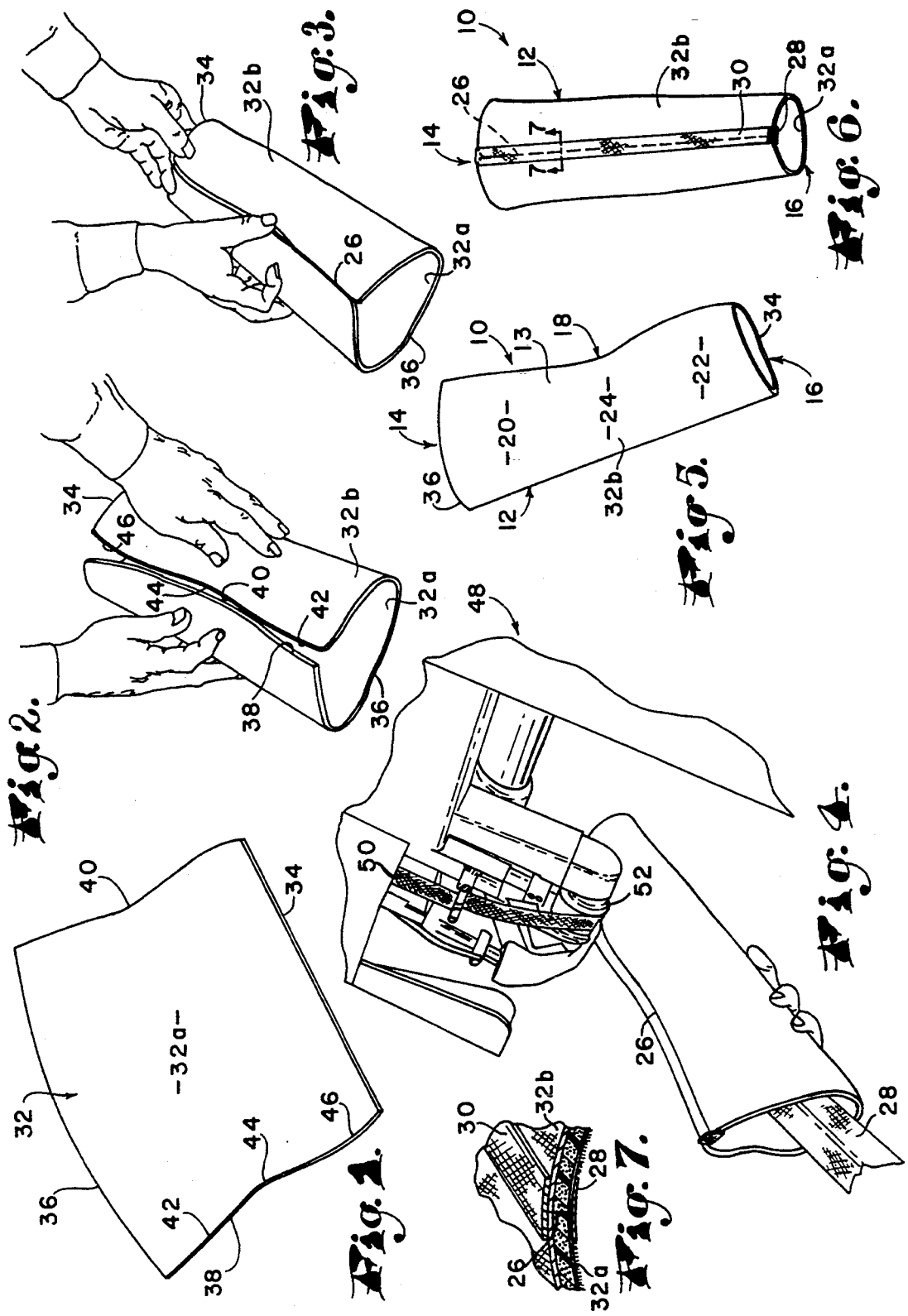

CONTOURED ORTHOPAEDIC SUPPORT HAVING REDUCED SKIN IRRITATION PROPERTIES

BACKGROUND OF THE INVENTION

1. Field of the Invention

The present invention is broadly concerned with improved, anatomically contoured orthopaedic supports, and methods of manufacture thereof, wherein the supports are entirely free of transversely extending dart-defining seams which can cause irritation over prolonged wearing periods. More particularly, it is concerned with an orthopaedic support of this type including an elongated, tubular body having a continuous sidewall, the latter presenting a recessed region intermediate the ends for anatomically conforming with a limb joint (e.g., knee or elbow) with complete elimination of potentially irritating transverse sewn seams in the recessed region.

2. Description of the Prior Art

Tubular orthopaedic supports of various types have long been produced and used by individuals to support a weak or injured limb during rehabilitation or as a general protective measure. To give but one example, knee supports are commonly used by athletes and include a elongated, tubular body adapted to be placed over the knee, lower thigh and upper calf regions of the leg. Such a knee support would typically include padding, lateral bracing and external straps permitting it to be properly positioned for maximum comfort and support. Modern day orthopaedic appliances of this type are commonly fabricated using closed cell neoprene rubber sleeves, which may be lined with a soft terry or nylon fabric.

Orthopaedic supports as described above can be in the form of simple tubular or frustoconical, open-ended bodies. These units are considered rather crude, however, and suffer from the problem of gathering at the limb joint or, in the case of a knee support, falling during exercise. It has also been known in the past to provide anatomically contoured supports which are designed to more closely conform with a limb joint. Again using the exemplary case of a knee support, anatomically contoured supports would generally include an outwardly flaring upper section designed to receive the lower thigh, a recessed central portion, and a lower, diverging, arcuate calf-receiving section. Contoured supports of this type are generally preferred, in that they largely avoid the problems of simple tubular designs.

However, conventional anatomically contoured tubular orthopaedic supports also present a significant problem in their own right. Specifically, these units are without known exception constructed from sheet material which is joined to form a tubular section. In order to achieve the recessed knee-receiving configuration though, it is essential that the sheet material be cut to form transverse darts. The transversely extending side margins of these dart cuts must consequently be connected to complete the contoured support, usually by stitching. The presence of these darts in the recessed region of the contoured support creates a very significant irritation factor for the user. That is, these transverse seams tend to rub and irritate the popliteal region of the knee joint during walking or exercise. It is not uncommon for users of such supports to suffer from soreness and/or skin abrasions in the popliteal region because of the transverse darts of conventional anatomically contoured knee supports.

There is accordingly a real and unsatisfied need in the art for an improved orthopaedic support which is not only anatomically contoured to conform with a limb joint, but which also eliminates dart-defining transverse seams at the recessed joint-receiving region thereof.

SUMMARY OF THE INVENTION

The present invention overcomes the problems outlined above, and provides a greatly improved orthopaedic support which completely eliminates the skin irritation problems associated with lateral dart seams. The supports of the invention are in the form of an elongated, tubular bodies each having a continuous sidewall and a pair of opposed, open ends, with the sidewall presenting a recessed region intermediate the ends for anatomically conforming with a limb joint. The sidewall is moreover completely free of dart-defining seams transverse to the longitudinal axis of the body at the recessed joint region.

In preferred forms, the support-defining sidewall includes only a single seam extending longitudinally along the length of the body, with this seam being entirely free of stitching. This assures that the supports of the invention are even more comfortable and free of potential skin irritation. To this end, the supports are advantageously formed from a single piece blank of soft, resilient material such as fabric-faced closed cell neoprene rubber; the side margins of the blank are first adhesively secured, and thereafter the resultant adhesive seam is covered inside and out by synthetic resin tape. After formation of this tubular support body, conventional appliances such as side braces or tightening straps can be connected to the support body, thereby forming a complete orthopaedic support.

BRIEF DESCRIPTION OF THE DRAWINGS

FIG. 1 is a perspective view of a neoprene rubber blank used in the formation of a contoured knee support in accordance with the invention;

FIGS. 2 and 3 are elevational views illustrating the first step in the manufacturing procedure wherein the inwardly arcuate side margins of the blank are drawn together and adhesively secured;

FIG. 4 is a fragmentary elevational view illustrating application of the preferred synthetic resin seam tape to the tubular blank;

FIG. 5 is a side view of the completed orthopaedic support, illustrating the anatomical contour thereof;

FIG. 6 is a rear view of the support illustrated in FIG. 5, showing the exterior seam tape; and FIG. 7 is a sectional view taken along line 7—7 of FIG. 6 and illustrating in detail the rear seam construction.

DETAILED DESCRIPTION OF THE PREFERRED EMBODIMENTS

Turning now to the drawings, and particularly FIGS. 5–7, an exemplary orthopaedic knee support 10 is illustrated. The support 10 is in the form of an elongated tubular body 12 presenting sidewall 13 with upper and lower, opposed, open ends 14, 16 with a recessed joint region 18 intermediate the ends 14, 16. It will be observed in this respect that the support 12 includes an uppermost, diverging, somewhat frustoconical section 20 adapted to receive and conform with the lower thigh; a lower, arcuate in side elevation section 22 for receiving and conforming with the upper calf; and a central knee section 24 bounded at the rear thereof by the recessed joint region 18 of the tubular body.

The body 12 is entirely integral save for a single joint or seam 26 extending between the ends 14, 16. Advantageously, this seam 26 is entirely free of stitching, and is formed by adhesive means only. As best illustrated in FIG. 7, the joint 26 is covered by internal and external synthetic resin seam tape sections 28, 30. It will be noted in this regard that the recessed region 18, which while in use is in close conforming contact with the popliteal region of the knee joint, has no transverse dart seams therein.

The tubular body 12 is preferably formed of closed cell neoprene rubber synthetic resin material, which has sufficient softness, resiliency and strength for this purpose. Normally, the inner and outer surfaces of the neoprene rubber are faced with fabric. In practice, use has been made of G-231-N and R-1400-N closed cell neoprene rubber sheeting commercialized by The Rubatex Corporation of Bedford, Va. This neoprene rubber is normally faced with stretch nylon on the surface thereof which forms the exterior of the final orthopaedic support; the opposed surface of the neoprene rubber presenting the interior surface of the final support can be faced with stretch nylon or stretch jersey fabric material (e.g., 900 standard light stretch jersey commercialized by Rubatex Corporation). Rubatex brochures entitled "Closed Cell Rubber and Plastic Sheets" and "Neoprene/Stretch Jersey Laminates" which describe and characterize the neoprene rubber material and fabric facings are incorporated by reference herein.

The synthetic resin seam tape section material is an adhesive backed nylon jersey material obtained from San Chemicals, Ltd., of Osaka, Japan, and is designated Melco T-5000. This seaming material is heat-applied and firmly bonds to the faced neoprene rubber in order to form a very secure final seam. A technical information brochure describing this seam tape material is incorporated herein by reference.

FIGS. 1-4 illustrate the preferred method of manufacture of the orthopaedic supports of the invention. In the first step, a sheet of the described, fabric-faced neoprene rubber is die cut to present a blank 32 depicted in FIG. 1. In the form shown, the blank has a stretched terry fabric inner surface 32a and a stretched nylon fabric outer surface 32b. The blank 32 presents a substantially rectilinear lower margin 34, an arcuate upper margin 36, and a pair of inwardly arcuate side margins 38, 40. Each of the side margins includes a generally straight upper segment 42 merging into an innermost, smoothly arcuate recessed zone 44. The lower section of each side margin extends outwardly from the zone 44 to a peak region 46, which then tails to intersect with lower margin 34.

After die cutting, an adhesive is applied to the side margins 38, 40. The preferred adhesive material is Rubatex R-27706 natural color adhesive which is designed for bonding neoprene rubbers and similar materials; a Rubatex technical data sheet pertaining to this adhesive is incorporated by reference herein. Once the adhesive is applied to the blank margins, the blank is manually folded together as shown in FIGS. 2 and 3, and the side margins 38 and 40 are adhered together in an abutting fashion. The preferred adhesive makes this a relatively simple and fast operation, and results in a completed tubular body having only the single, longitudinally extending seam 26.

Thereafter, the seam tape sections 28 and 30 are applied to the seam 26 to complete the support. FIG. 4 illustrates this operation and the use of commercially available bonding equipment 48. The latter includes a supply 50 of the seam tape, which extends around a heated roller 52. In addition, hot air from a source not shown is directed onto the seaming tape as it is applied to the seam 26. The roller 52 is normally maintained at a temperature of around 275°-280° F., while the hot air is normally maintained at a level of about 400° F. This heat application of the tape sections is rapidly carried out on both the inside and outside of the support. It will be understood in this respect that the outside section 30 is normally first applied, whereupon the body 12 is turned inside out, and the inner seam tape section 28 is applied. Equipment of the general type illustrated in FIG. 4 can be obtained from a number of sources, e.g., the Sunbrand Division of Wilcox & Gibbs, Inc. of Atlanta, Ga. A manufacturer's brochure describing equipment of this character, and particularly Models 8304 and 8309 is incorporated by reference herein.

After fabrication of the support 10 as illustrated, the usual orthopaedic appliances such as tightening straps, additional padding, or rigid braces, can be readily affixed to the support. Such modifications are well within the skill of the art and need not be explained in detail.

The construction of support 10 also allows the body 12 to be cut as may be necessary to maximize the fit and comfort for a particular individual. Moreover, such adjusting cuts may be made through the seam 26, without detracting from the integrity of the remainder of the seam. This is to be contrasted with conventional sewn seams, where any cutting of the seam almost inevitably leads to unraveling.

I claim:

1. An orthopaedic support consisting essentially of an elongated, tubular body having a continuous sidewall and a pair of opposed, open ends, said sidewall presenting a recessed region intermediate said ends for anatomically conforming with a limb joint, said sidewall being free of dart-defining seams oriented transverse to the longitudinal axis of said body at said recessed region, said body being formed from a single piece, unitary blank presenting a pair of opposed, inwardly arcuate side margins, with said side margins being adhesively interconnected to give a single, elongated, axially extending seam which is essentially free of stitching, there being an elongated synthetic resin tape adhesively secured over at least one face of said seam.

2. The orthopaedic support of claim 1, said body being formed of closed cell neoprene rubber synthetic resin material.

3. The orthopaedic support of claim 2, said neoprene rubber synthetic resin material having a jersey inner lining.

4. The orthopaedic support of claim 1, including synthetic resin tape adhesively secured to both faces of said seam.

5. The orthopaedic support of claim 1, said support being a knee support and presenting an upper thigh-receiving section, a lower, anatomically contoured, calf-receiving region, and an intermediate, recessed knee-receiving region presenting a rearmost section conforming to the popliteal region of the knee.

* * * * *